United States Patent
Hiramura et al.

(10) Patent No.: US 9,974,738 B2
(45) Date of Patent: May 22, 2018

(54) DISINTEGRATING PARTICLE COMPOSITION PRODUCED BY TWO-STAGE WET GRANULATION PROCESS, AND INTRAORALLY DISINTEGRATING TABLET CONTAINING SAME COMPOSITION

(71) Applicant: DAICEL CORPORATION, Osaka-shi, Osaka (JP)

(72) Inventors: Takahiro Hiramura, Tokyo (JP); Kiyoshi Ikura, Himeji (JP); Sae Itaya, Himeji (JP); Tomohito Okabayashi, Himeji (JP); Naohiro Hashikawa, Himeji (JP); Anan Sakaguchi, Himeji (JP)

(73) Assignee: DAICEL CORPORATION, Osaka-Shi, Osaka (JP)

( * ) Notice: Subject to any disclaimer, the term of this patent is extended or adjusted under 35 U.S.C. 154(b) by 0 days. days.

(21) Appl. No.: 15/021,647

(22) PCT Filed: Sep. 24, 2014

(86) PCT No.: PCT/JP2014/075241
§ 371 (c)(1),
(2) Date: Apr. 11, 2016

(87) PCT Pub. No.: WO2015/046223
PCT Pub. Date: Apr. 2, 2015

(65) Prior Publication Data
US 2016/0250144 A1 Sep. 1, 2016

(30) Foreign Application Priority Data
Sep. 27, 2013 (JP) .................... 2013-202248

(51) Int. Cl.
A61K 9/20 (2006.01)
A61K 9/00 (2006.01)
A61K 9/16 (2006.01)

(52) U.S. Cl.
CPC .......... *A61K 9/0056* (2013.01); *A61K 9/1635* (2013.01); *A61K 9/1652* (2013.01); *A61K 9/1694* (2013.01); *A61K 9/2054* (2013.01)

(58) Field of Classification Search
CPC .......................... A61K 9/2054; A61K 9/0056
See application file for complete search history.

(56) References Cited

U.S. PATENT DOCUMENTS 2,851,453 A * 9/1958 Kennon .................. C08B 11/20
424/DIG. 14
2011/0150989 A1 6/2011 Park et al.

FOREIGN PATENT DOCUMENTS

EP 1 980 272 10/2008
EP 2 251 005 11/2010
(Continued)

OTHER PUBLICATIONS

International Search Report of International Application No. PCT/JP2014/067936 dated Aug. 12, 2014.
(Continued)

*Primary Examiner* — Carlos A Azpuru
(74) *Attorney, Agent, or Firm* — Ping Wang; Morris, Manning & Martin LLP

(57) ABSTRACT

A method is used in the production of a disintegrative particulate composition including three components consisting of a first disintegrator component having sedimentation volume in water of 4.0 cm³/g or more, and a second disintegrator component other than the first disintegrator component and an excipient. The method includes a first wet granulation step using any two of the three components, and a second wet granulation step using the granules obtained in
(Continued)

the first wet granulation step and at least the component not used in the first wet granulation step; thus the disintegrative particulate composition is produced. Moreover, an orally disintegrating tablet contains a medicinal ingredient and the disintegrative particulate composition.

12 Claims, 1 Drawing Sheet

(56) References Cited

FOREIGN PATENT DOCUMENTS

| | | | |
|---|---|---|---|
| EP | 2 368 544 | | 9/2011 |
| EP | 3 050 560 | | 8/2016 |
| JP | 10-182436 | | 7/1998 |
| JP | 2000-273039 | | 10/2000 |
| JP | 2002-179558 | * | 6/2002 |
| JP | 2007153887 | | 6/2007 |
| JP | 2008-285434 | * | 11/2008 |
| JP | 4551627 | | 9/2009 |
| JP | 2010529074 | | 8/2010 |
| JP | 2012-31138 | | 2/2012 |
| JP | 2012-188364 | | 10/2012 |
| JP | 2012-188364 A | * | 10/2012 |
| JP | 2013-147470 | | 8/2013 |
| WO | 2007/01892 A1 | * | 2/2007 |
| WO | 2007/018192 | | 2/2007 |
| WO | 2009/102038 | | 8/2009 |
| WO | 2009107864 | | 9/2009 |
| WO | 2011/019045 | | 2/2011 |
| WO | 2012/087377 | | 6/2012 |
| WO | 2013100701 | | 7/2013 |
| WO | 2013/146917 | | 10/2013 |
| WO | 2014/046035 | | 3/2014 |

OTHER PUBLICATIONS

International Search Report of International Application No. PCT/JP2013/059083 dated Jun. 25, 2013.
International Search Report of International Application No. PCT/JP2013/074823 dated Sep. 13, 2013.
International Search Report of International Application No. PCT/JP2014/075241 dated Dec. 22, 2014.
Extended European Search Report of International Application No. 14848578.2 dated Jun. 2, 2017.
U.S. Appl. No. 14/384,358, filed Oct. 11, 2014, Pending.
U.S. Appl. No. 14/426,669, filed Mar. 6, 2015, Pending.
U.S. Appl. No. 14/898,423, filed Dec. 14, 2015, Pending.
U.S. Appl. No. 14/915,872, filed Mar. 11, 2016, Pending.

* cited by examiner

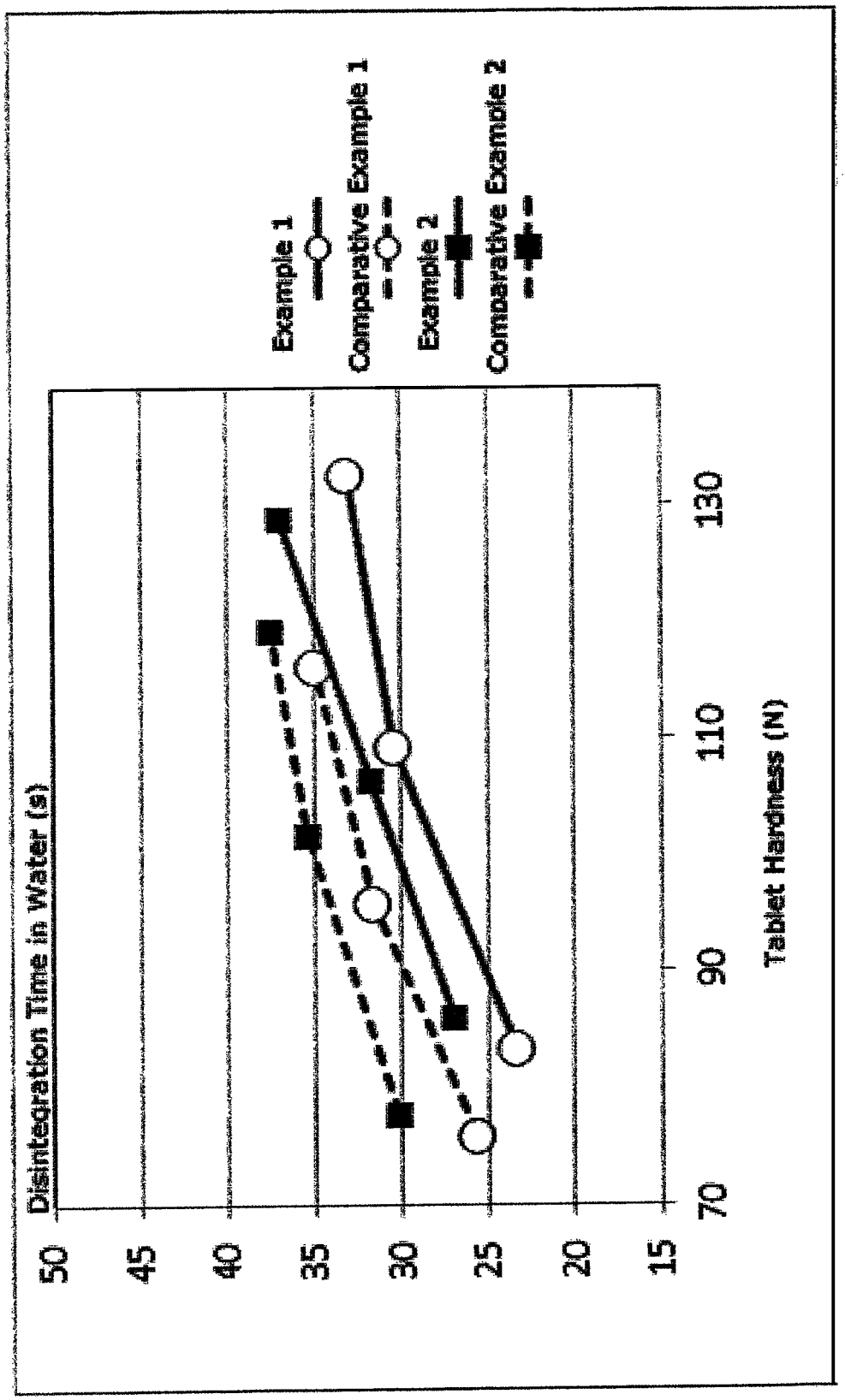

DISINTEGRATING PARTICLE COMPOSITION PRODUCED BY TWO-STAGE WET GRANULATION PROCESS, AND INTRAORALLY DISINTEGRATING TABLET CONTAINING SAME COMPOSITION

TECHNICAL FIELD

The present invention relates to a disintegrative particulate composition produced by a two-stage granulation process, an orally disintegrating tablet comprising said composition and the like.

BACKGROUND ART

In the past, orally disintegrating tablets have been developed as highly convenient forms which can safely be taken by patients who have difficulty in swallowing drugs, elderly people, children, etc., and which can easily be taken without water. In addition to the need by said people, the need for the orally disintegrating tablets has been increased in the field of health food products, for example, in the situation where the convenience of taking without water can be utilized such as a supplement tablet for athletes during exercise. It is important, that the orally disintegrating tablets have sufficient breaking strength (tablet hardness) such that any cracks, powdering, etc. are not caused in the tablets during production or transportation of the tablets or during breaking their seals in the same manner as general tablets, and also, it is important that the orally disintegrating tablets have excellent disintegrability (disintegration time) such that the tablets immediately disintegrate in the oral cavity.

An excellent moldability will be required in the production of a tablet. The moldability means the relation between a tablet compression force and the tablet hardness obtained thereby. A process that needs a high tablet compression force could cause problems such as limitation in the performance of a tablet-compressing machine, reduction of productivity and reduction in the properties of coating particles comprised in the tablet. It will be therefore important for the particle or particulate composition constituting the tablet to have such an excellent moldability that a higher tablet hardness can be obtained with the same tablet compression force, or that the same tablet hardness can be obtained by a lower tablet compression force.

The tablet hardness and disintegrability are mutually opposing properties. In general, when a molding pressure is increased to increase the hardness, the disintegration time will tend to be prolonged, and, when the molding pressure is reduced to shorten the disintegration time, the hardness will tend to be smaller. Therefore, various technologies have been developed in order to cope with both the two properties or to achieve an optimal balance between the two properties.

Furthermore, the components of particles, granulation methods, etc. have been studied in order to impart superior moldability to the particles or particulate compositions constituting tablets.

For example, Patent Literature (PTL) 1 discloses a disintegrative particulate composition that is produced by homogeneously dispersing mannitol, xylitol, inorganic excipient, disintegrator and carmellose in the presence of water, followed by drying. The composition is characterized in that xylitol is solid-dispersed in mannitol particles to form composite particles, and that inorganic excipient, disintegrator and carmellose are dispersed in the composite particles. Said disintegrative particulate composition is produced by spray-granulation of the dispersion wherein the above components are dispersed in aqueous solvent or by spraying to carriers made of mannitol and the like.

PTL 2 discloses an orally disintegrating tablet comprising carboxymethylcellulose in an amount of 10% (w/w) or more based on the total amount including medicinal ingredients. It is produced by mixing each component, followed by formulation with a tableting machine.

PTL 3 discloses a method for the production of an orally disintegrating tablet comprising loratadine as a medicinal ingredient. The method include two granulation steps, wherein loratadine is granulated with at least one of additives such as a binder, excipient, disintegrator and the like in a first granulation step, and the resulting granules obtained in the first granulation step is further granulated with at least one of the same additives as in the first step. Carmellose is listed as an example of the disintegrator.

Furthermore, PTL 4 discloses a method for the production of an orally disintegrating tablet. The method comprises a step of spraying an aqueous suspension of a water-soluble and hydrophilic disintegrator onto a mixture of a medicinal ingredient and an excipient to give a granulate (A) comprising the medicinal ingredient, and a step of spraying an aqueous suspension of the same water-soluble and hydrophilic disintegrator as above onto the excipient to give a granulate (B) without the medicinal ingredient, and a step of compression molding of the granulates (A) and (B).

RELATED ARTS

Patent Literatures

PTL 1: International Publication Pamphlet WO2011/019045
PTL 2: JP-A-2008-285434
PTL 3: JP-A-2012-31138
PTL 4: Specification of Japanese Patent No. 4551627

SUMMARY OF INVENTION

Problems to be Solved by the Invention

The problems to be solved by the present invention is to provide a method for the production of a disintegrative particulate composition comprising first and second integrator components, which can provide an orally disintegrating tablet with the composition with both an excellent tablet hardness and disintegrability when it is added to the orally disintegrating tablet.

Means to Solve the Problem

The present inventors have earnestly studied and found that the above problems can be solved by using a method for the production of a disintegrative particulate composition including three components consisting of a first disintegrator component having sedimentation volume in water of 4.0 cm3/g or more, a second disintegrator component other than the first disintegrator component and an excipient, which comprises a first wet granulation step using any two of the three components and a second wet granulation step using the granules obtained in the first wet granulation step and at least the remaining one component not used in the first wet granulation step.

Thus, the present invention relates to the following aspects.

Aspect 1

A method for the production of a disintegrative particulate composition including three components consisting of a first disintegrator component having sedimentation volume in water of 4.0 cm³/g or more, a second disintegrator component other than the first disintegrator component and an excipient, which comprises a first wet granulation step using any two of the three components and a second wet granulation step using the granules obtained in the first wet granulation step and at least the remaining one component not used in the first wet granulation step.

Aspect 2

The method according to Aspect 1, wherein the first disintegrator component is crospovidone, croscarmellose sodium, carboxymethyl starch sodium, carboxymethylcellulose calcium, α-starch or partially α-starch.

Aspect 3

The method according to Aspect 2, wherein the first disintegrator component is crospovidone.

Aspect 4

The method according to one of Aspects 1 to 3, wherein the second disintegrator components are one or more of non-α-starch, corn starch, processed starch, hydroxypropyl starch and low substituted hydroxypropylcellulose.

Aspect 5

The method according to one of Aspects 1 to 4, wherein crystalline cellulose is used as a forth component in the first wet granulation step and/or the second wet granulation step.

Aspect 6

A disintegrative particulate composition produced by the method according to one of Aspects 1 to 5.

Aspect 7

An orally disintegrating tablet comprising a medicinal ingredient and the disintegrative particulate composition according to aspect 6.

Advantageous Effects of Invention

By producing a disintegrative particulate composition including three components consisting of a first disintegrator component having sedimentation volume in water of 4.0 cm³/g or more, a second disintegrator component other than the first disintegrator component and an excipient according to a method that comprises particular two steps, it is possible to produce a disintegrative particulate composition that provides more excellent tablet hardness and disintegrability than those of the disintegrative particulate composition including the same components but produced by a method using said three components together in one granulation step.

BRIEF DESCRIPTION OF THE DRAWINGS

FIG. 1 shows tablet hardness and disintegration time in water of each tablet obtained in Examples and Comparative Examples.

DESCRIPTION OF EMBODIMENTS

The present invention relates to the method for the production of the disintegrative particulate composition including three components consisting of the first disintegrator component having sedimentation volume in water of 4.0 cm3/g or more, the second disintegrator component other than the first disintegrator component and the excipient, which is characterized by comprising the first wet granulation step using any two of the three components and the second wet granulation step using the granules obtained in the first wet granulation step and at least the remaining one component not used in the first wet granulation step. The second wet granulation step may use the granules obtained in the first wet granulation step and only the remaining one component not used in the first wet granulation step.

Four mechanisms of "wicking", "swelling", "deformation" and "repulsion" have been proposed as mechanisms of disintegration of tablets or the like. Among them, "swelling" is a disintegration mechanism which proceeds upon swelling of disintegrators themselves as a result of water permeation through the disintegrators.

The first disintegrator component included in the disintegrative particulate composition according to the present invention is characterized by having sedimentation volume in water of 4.0 cm³/g or more. The sedimentation volume in water of the disintegrator component is a value determined according to the following method.

[Method for the Determination of Sedimentation Volume in Water]

A disintegrator component (1.0 g) was gradually added to a beaker containing s purified water of 75 mL while being stirred with a stirrer. After the completion of addition of the whole volume of the disintegrator component, it is stirred for 3 min. The resulting suspension is then transferred to a measuring cylinder (100 mL), diluted in the measuring cylinder to 100 mL, and allowed to stand still for 16 hours, followed by measuring the sedimentation volume.

Values of the sedimentation volume determined by the above method are shown in Table 1 for representative examples of the disintegrator components. As the sedimentation volume of the disintegrator component is correlated with its swelling property, it is estimated that the larger is the sedimentation volume of the disintegrator component, the higher is its swelling property.

Thus, it is preferable to use as the first disintegrator component one that is high in swelling property, that is, superior in the effect of promoting swelling. Preferable examples of such disintegrator component include crospovidone, croscarmellose sodium, carboxymethyl starch sodium, carboxymethylcellulose calcium, alpha-starch or partially alpha-starch. Crospovidone, which is a popular name of a cross-linked polymer of 1-vinyl-2-pyrrolidone, is more preferable. Croscarmellose sodium is a popular name for a cross-liked product of carboxymethylcellulose sodium.

As the second disintegrator component are listed one or more of non-alpha-starch, corn starch, processed starch, hydroxypropyl starch and low substituted hydroxypropylcellulose.

Acid-type carboxymethylcellulose is a substance called carmellose. In some cases, a salt of carboxymethylcellulose may be referred to as carmellose. Although such carmellose is included in some of the conventional tablets as the disintegrator, it is preferable not to be included in the disintegrative particulate composition according to the present invention.

Table 1 shows the sedimentation volumes (swelling property) in water of the representative examples of the disintegrator components, which were determined by the above method.

TABLE 1

| Disintegrator Component | Sedimentation Volume in Water (cm$^3$/g) |
|---|---|
| Corn starch | 1.5 |
| Hydroxypropyl starch | 1.5 |
| Carmellose | 2.5 |
| Crospovidone | 6.0 |
| Croscarmellose sodium | 14 |
| Carboxymethyl starch sodium | 26 |
| Carboxymethylcellulose calcium | 9.5 |
| Alpha-starch | 14 |
| Partially alpha-starch | 8.0 |

Any compound which has been known to those skilled in the art as an excipient may be included as the third component in the disintegrative particulate composition of the present invention. Typical examples of such a compound include sugars or sugar alcohols such as mannitol, erythritol, sorbitol, D-glucitol (maltitol), xylitol, trehalose, lactose and maltose. Moreover, as preferable examples thereof, mannitol, erythritol, trehalose, sorbitol and D-glucitol (maltitol) can be mentioned. As the excipient, two or more types of compounds properly selected from these compounds can also be used. Furthermore, when excipients are used in each of the first and second wet granulation steps, the excipients may be of the same type (the same combination), or may be of different types (different combinations).

The disintegrative particulate composition produced by the method of the present invention can include a crystalline cellulose known to those skilled in the art, as the fourth component. As typical examples of such a crystalline cellulose, commercially-available products such as "Avicel" (FMC Corporation), "CEOLUS" (Asahi Kasei Chemicals Corp.), and "VIVAPUR" (RETTENMAIER) can be mentioned.

Furthermore, various types of optional components known to those skilled in the art may properly be added and mixed into the disintegrative particulate composition of the present invention, for the purpose of adjusting various characteristics such as the disintegrating force, binding force and ease in taking the tablet, without impairing the effects of the present invention according to the above-described three or four components. As examples of such components, fluidizing agents, inorganic excipients, sweetening agents, flavoring agents and coloring agents can be mentioned.

The amount of each component blended in the disintegrative particulate composition of the present invention can properly be determined by those skilled in the art, depending on, for example, the type of the component, the type and purpose of the medicinal ingredient, which is a target to be used in the disintegrative particulate composition, or the purpose of the final product, i.e. the orally-disintegrating tablet. In general, relative to the total weight of the disintegrative particulate composition, the amount of the first disintegrator component is within a range of 1% to 30% by weight, the amount of the second disintegrator component is within a range of 1% to 30% by weight, and the amount of the excipient is within a range of 40% to 98% by weight, which are a total amount used in the first and/or second wet granulation steps.

The first and second granulation steps of the method according to the present invention are carried out by a method in which each component is dispersed in the presence of water, and the dispersion is dried to form complexes, i.e. by a wet granulation process. As specific examples of the wet granulation process, spray methods such as spray drying, tumbling granulation, agitation granulation and fluidized-bed granulation, the freeze-drying method, kneading granulation, and the like can be mentioned, and the composition can be produced by any of these methods known to a person skilled in the art.

Since disintegrators are generally hydrophilic, by carrying out a manipulation of applying a physical force such as by agitation or the like in the presence of water according to wet granulation, the aggregated state in the dry powder converts into a state in which particles are more dispersed. Dispersion can most easily be carried out by the fluidized-bed granulation process, spray drying, tumbling granulation, agitation granulation, etc., in which dispersion by water spraying and drying are carried out, and also, drying speeds in these methods are high. Therefore, these methods are preferable.

Among them, the fluidized-bed granulation process is a granulation method in which water, an aqueous solution including a binder, or the like is sprayed onto powder, while blowing the powder up by hot air, and, for example, adjustment of spraying conditions, etc. is easy in this method. Therefore, the fluidized-bed granulation process is the most preferable method.

Those skilled in the art can properly determine which two types of the components among the three components are used in the first wet granulation step of the present, depending on their types, amounts, etc. For example, the first wet granulation step can be carried out by using one of the first or second disintegrator component, and the excipient, and the other disintegrator component can be added in the second wet granulation step. Alternatively, the first wet granulation step can be carried out by using both the first and second disintegrator components, and the excipient can be added in the second wet granulation step. The crystalline cellulose can be optionally added in the first and/or second wet granulation step.

Various types of the optional components, other than the above-described components, which can be appropriately included in the disintegrative particulate composition of the present invention and which have been known to those skilled in the art, may be properly added in the first and/or second wet granulation step. Alternatively, these optional components may also be added and mixed in an appropriate granulation step of the third step or subsequent steps.

Furthermore, those skilled in the art can properly determine various conditions such as the spraying speed, the supply air temperature, the exhaust temperature, and the air supply rate, depending on types or amounts of components, etc.

In both of the first wet granulation step and the second wet granulation step according to the fluidized-bed granulation process, as a medium for the spray liquid, a solvent acceptable in pharmaceuticals or foods, such as water, ethanol, methanol or acetone, can be mentioned. Alternatively, as the spray liquid, for example, an aqueous solution in which less than 10% of the component(s) for the disintegrative particulate composition is dissolved can be mentioned, and, in particular, water or such an aqueous solution is preferable.

The present invention relates also to the disintegrative particulate composition obtained by the method according to the present invention, and to the orally disintegrating tablet comprising a medicinal ingredient and said disintegrative particulate composition. The orally disintegrating tablet according to the present invention may optionally include other components acceptable as additives from a pharmaceutical or food-sanitary point of view, such as excipients, surfactants, lubricants, acidulants, sweeteners, corrigents, flavoring agents, colorants, and stabilizing agents, when needed. As these optional components, for example, appropriate ingredients described in "Japanese Pharmaceutical Excipients Directory" (YAKUJI NIPPO LIMITED) or the Japanese Pharmacopoeia; designated or existing additives according to Food Sanitation Law, Art. 10; natural flavor; and additives listed in a list of general additives for food and drink can be used. There is no limitation in the kind of the medicinal ingredient and the above auxiliary agents. Also, the blending ratios of the disintegrative particulate composition, the medicinal ingredient and each optional ingredient (component) are not particularly limited as long as the expected effects of the present invention are brought about, and the blending ratios can properly be determined by those skilled in the art. The orally disintegrating tablet can be formulated by any methods known to those skilled in the art, for example, by tableting.

It is preferable that the disintegrative particulate composition of the present invention have the following physical properties:
(1) an average particle size of 70 to 110 microns; and
(2) a water content of 2% to 6% by weight.

In addition, these physical properties are measured by using the following methods and conditions.

The average particle size: 2 g of the disintegrative particulate composition is subjected to a measurement with a Φ75 mm automatic shaking sieve device (Type "M-2", Tsutsui Scientific Instruments Co., Ltd.).

The water content: 5 g of the disintegrative particulate composition is subjected to a measurement using a halogen water content measuring device (Type "HB43", METTLER TOLEDO K.K.).

The orally-disintegrating tablet of the present invention may have a hardness of 50 to 150 N and a disintegration time in water of 10 to 60 seconds, preferably have 80 to 150 N and a disintegration time in water of 10 to 30 seconds.

In addition, contents of all related art documents cited in the present specification are incorporated herein by reference.

Hereinafter, the present invention will more specifically be described with reference to Examples. However, the present invention is not considered to be limited to the Examples.

EXAMPLES

Example 1

As the first wet granulation step, 285 g of mannitol (D-mannitol, Merck Ltd.), 75 g of cornstarch (an official drug included in Japanese Pharmacopoeia; NIHON SHOKUHIN KAKO CO., LTD.) and 100 g of a crystalline cellulose (CEOLUS PH-101, Asahi Kasei Chemicals Corp.) were charged to a fluidized-bed granulator (FL-LABO, Freund Corporation), and 150 g of purified water was sprayed onto the resulting mixture at a rate of 5~15 g/minute to thereby granulate the mixture. Further, as the second wet granulation step, 40 g of crospovidone (Polyplasdone INF-10, ISP Japan) was added to the resulting granules, and 80 g of purified water was sprayed thereto at 4 g/minute to thereby obtain granules (a disintegrative particulate composition of the present invention). 0.5 parts by weight of magnesium stearate (Taihei Chemical Industrial Co. Ltd.) was added to 99.5 parts by weight of the obtained granules, and these were mixed. The mixture was then subjected to tableting at tablet compression forces of 6.0, 8.0 and 10.0 kN with a simple tableting machine (HANDTAB-100, ICHI-HASHI-SEIKI Co., Ltd.) to thereby obtain an angled-corner flat tablet having a diameter of 8.0 mm and a weight of 250 mg. In addition, the granules had the following values for physical properties: (1) an average particle size of 89 microns and (2) a water content of 3.4% by weight.

Example 2

As the first wet granulation step, 224 g of mannitol (D-mannitol, Merck Ltd.), 80 g of hydroxypropyl starch (HPS-101W, Freund Corporation) and 80 g of the crystalline cellulose (CEOLUS PH-101, Asahi Kasei Chemicals Corp.) were charged to the fluidized-bed granulator (FL-LABO, Freund Corporation), and 120 g of purified water was sprayed onto the resulting mixture at a rate of 5 g/minute to thereby granulate the mixture. Further, as the second wet granulation step, 16 g of crospovidone (Polyplasdone INF-10, ISP Japan) was added to the resulting granules, and 80 g of purified water was sprayed thereto at 2~5 g/minute to thereby obtain granules (a disintegrative particulate composition of the present invention). The resulting granules were subjected to tableting in the same manner as in Example 1 to thereby obtain an angled-corner flat tablet having a diameter of 8.0 mm and a weight of 250 mg. In addition, the granules had the following values for physical properties: (1) an average particle size of 84 microns and (2) a water content of 3.5% by weight.

Comparative Example 1

As the first wet granulation step, 285 g of mannitol (D-mannitol, Merck Ltd.), 75 g of corn starch (official drug included in Japanese Pharmacopoeia; NIHON SHOKUHIN KAKO CO., LTD.), 100 g of the crystalline cellulose (CEOLUS PH-101, Asahi Kasei Chemicals Corp.) and 40 g of crospovidone (Polyplasdone INF-10, ISP Japan) were charged to the fluidized-bed granulator (FL-LABO, Freund Corporation), and 80 g of purified water was sprayed onto the resulting mixture at a rate of 4 g/minute to thereby obtain granules. The resulting granules were subjected to tableting in the same manner as in Example 1 to thereby obtain an angled-corner flat tablet having a diameter of 8.0 mm and a weight of 250 mg. In addition, the granules had the following values for physical properties: (1) an average particle size of 70 microns and (2) a water content of 3.8% by weight.

Comparative Example 2

As the first wet granulation step, 224 g of mannitol (D-mannitol, Merck Ltd.), 80 g of hydroxypropyl starch (HPS-101W, Freund Corporation), 80 g of the crystalline cellulose (CEOLUS PH-101, Asahi Kasei Chemicals Corp.) and 16 g of crospovidone (Polyplasdone INF-10, ISP Japan) were charged to the fluidized-bed granulator (FL-LABO, Freund Corporation), and 80 g of purified water was sprayed onto the resulting mixture at a rate of 4.6 g/minute to thereby obtain granules. The resulting granules were subjected to tableting in the same manner as in Example 1 to thereby obtain an angled-corner flat tablet having a diameter of 8.0 mm and a weight of 250 mg. In addition, the granules had the following values for physical properties: (1) an average particle size of 88 microns and (2) a water content of 3.7% by weight.

[Evaluation on Hardness and Disintegrability Tests]

Hardness and disintegrability of the tablets obtained in Examples and Comparative Examples were measured by following methods. The test results of hardness and disintegration time are shown in Table 2 and FIG. 1.

The values of the physical properties of the resulting tablets were measured based on the following conditions/methods.

Hardness: a hardness (N) was measured with a digital Kiya hardness tester (Fujiwara Scientific Company Co., Ltd.).

Disintegration time in water: a disintegration time in water was measured with a disintegration tester (NT-400, TOYAMA SANGYO CO., LTD.) in accordance with the method described in the Japanese Pharmacopoeia provided that an auxiliary disk was not used.

The measurements for the hardness and disintegration time were each repeated six times, and average values thereof were regarded as measurement results.

TABLE 2

| Tablet | Example 1 | | | Comparative Example 1 | | |
|---|---|---|---|---|---|---|
| Tablet Compression Force (kN) | 6.0 | 8.0 | 10.0 | 6.0 | 8.0 | 10.0 |
| Tablet Hardness (N) | 83 | 109 | 133 | 76 | 96 | 116 |
| Disintegration Time in Water(s) | 23 | 31 | 33 | 26 | 32 | 35 |

| Tablet | Example 2 | | | Comparative Example 2 | | |
|---|---|---|---|---|---|---|
| Tablet Compression Force (kN) | 6.0 | 8.0 | 10.0 | 6.0 | 8.0 | 10.0 |
| Tablet Hardness (N) | 86 | 106 | 129 | 78 | 101 | 119 |
| Disintegration Time in Water(s) | 27 | 32 | 37 | 30 | 35 | 38 |

The results shown in Table 2 demonstrate that the orally disintegrating tablet produced by the two-stage granulation process in Example 1 has more excellent disintegrability in spite of a high tablet hardness when compared with that produced in Comparative Example (one-stage granulation process).

The same results are obtained in Example 2 and Comparative Example 2.

INDUSTRIAL APPLICABILITY

The present invention significantly contributes to research and development of orally-disintegrating tablets having excellent tablet hardness and disintegrability.

The invention claimed is:

1. A method for the production of a disintegrative particulate composition including three components consisting of (1) a first disintegrator component having sedimentation volume in water of 4.0 cm$^3$/g or more, (2) a second disintegrator component other than the first disintegrator component, wherein the first and second disintegrator component are not an acid-type carboxylmethylcellulose, and (3) an excipient component,
   wherein the method comprises:
   a first wet granulation step using any two of the three components; and
   a second wet granulation step using at least the granules obtained in the first wet granulation step and the other one of the three components which is not used in the first wet granulation step.

2. The method according to claim 1, wherein the first disintegrator component is crospovidone, croscarmellose sodium, carboxymethyl starch sodium, carboxymethylcellulose calcium, alpha-starch or partially alpha-starch.

3. The method according to claim 2, wherein the first disintegrator component is crospovidone.

4. The method according to claim 1, wherein the second disintegrator components are one or more of non- alpha-starch, corn starch, processed starch, hydroxypropyl starch and low substituted hydroxypropylcellulose.

5. The method according to claim 1, wherein crystalline cellulose is used as a forth component in the first wet granulation step and/or the second wet granulation step.

6. A disintegrative particulate composition produced by the method according to claim 1.

7. An orally disintegrating tablet comprising a medicinal ingredient and the disintegrative particulate composition according to claim 6.

8. The method according to claim 2, wherein the second disintegrator components are one or more of non- alpha-starch, corn starch, processed starch, hydroxypropyl starch and low substituted hydroxypropylcellulose.

9. The method according to claim 3, wherein the second disintegrator components are one or more of non- alpha-starch, corn starch, processed starch, hydroxypropyl starch and low substituted hydroxypropylcellulose.

10. The method according to claim 2, wherein crystalline cellulose is used as a forth component in the first wet granulation step and/or the second wet granulation step.

11. The method according to claim 3, wherein crystalline cellulose is used as a forth component in the first wet granulation step and/or the second wet granulation step.

12. The method according to claim 4, wherein crystalline cellulose is used as a forth component in the first wet granulation step and/or the second wet granulation step.

* * * * *